United States Patent [19]
Mahoney

[11] 4,106,001
[45] Aug. 8, 1978

[54] MOISTURE DETECTOR

[76] Inventor: Kurt Mahoney, 2600 E. Southern Ave., Tempe, Ariz. 85282

[21] Appl. No.: 796,130

[22] Filed: May 12, 1977

[51] Int. Cl.² .......................................... G08B 21/00
[52] U.S. Cl. ................. 340/604; 128/138 A; 340/573
[58] Field of Search .............. 340/235, 244 C; 128/138 A

[56] References Cited

U.S. PATENT DOCUMENTS

| | | | |
|---|---|---|---|
| 2,874,695 | 2/1959 | Vaniman | 128/138 A |
| 3,460,123 | 8/1969 | Bass | 340/235 |
| 3,732,556 | 5/1973 | Caprillo et al. | 340/244 C |
| 3,778,570 | 12/1973 | Shuman | 340/235 |
| 3,832,993 | 9/1974 | Clipp | 128/138 A |
| 3,864,676 | 2/1975 | Macias et al. | 128/138 A |
| 3,939,360 | 2/1976 | Jackson | 340/244 C |

*Primary Examiner*—John W. Caldwell, Sr.
*Assistant Examiner*—Daniel Myer
*Attorney, Agent, or Firm*—Warren F. B. Lindsley

[57] ABSTRACT

A garment clip on device having a housing contoured on its outer surface to provide an indentation for receiving therein and holding a thin narrow adhesively coated wrap-around strip containing spaced apart conductors which when bridged by urination energize an alarm system mounted within the housing.

8 Claims, 6 Drawing Figures

U.S. Patent   Aug. 8, 1978   4,106,001
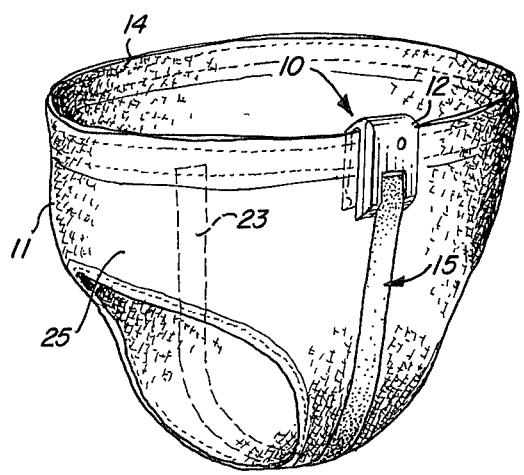
FIG-1
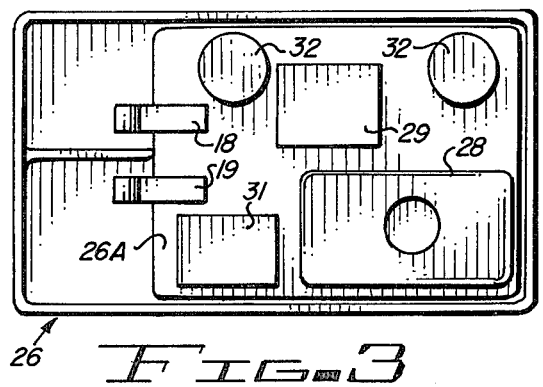
FIG-3
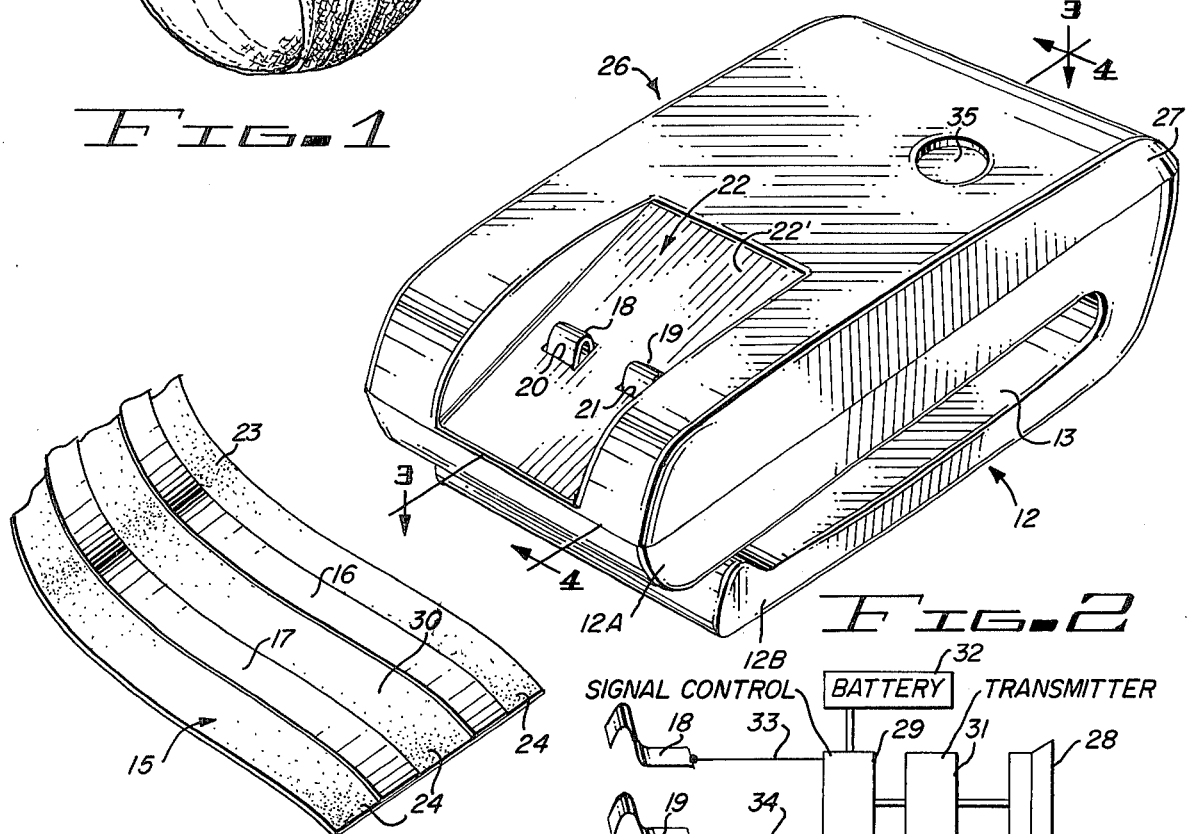
FIG-5
FIG-2
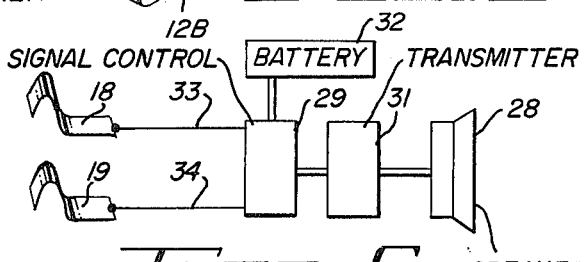
FIG-6
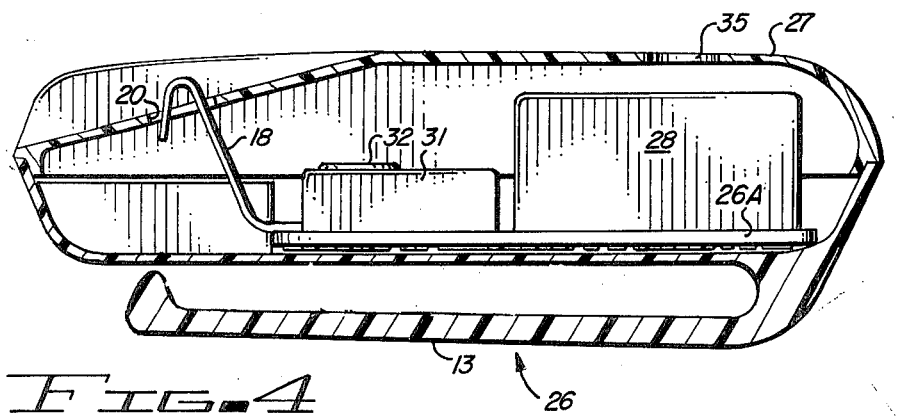
FIG-4

MOISTURE DETECTOR

BACKGROUND OF THE INVENTION

This invention relates to devices for detecting unintentional urination and, more particularly, to an improved detachably mountable and replaceable elongated strip detector.

DESCRIPTION OF THE PRIOR ART

Numerous devices have been designed for use in detecting and signalling unintentional urination. In these prior devices the detector means has been expensive to manufacture and frequently uncomfortable to the wearer. In the expensive devices, electrodes are buried in a permanent reusable cover which, when wet, serves to complete the circuit of the electrodes. This type of device is difficult to maintain hygenically clean for reuse purposes. In other known constructions the electrodes are simply enclosed in a disposable cover without the use of the support for the electrodes and are not sufficiently resilient to retain their form with the result that it is uncomfortable to the wearer.

SUMMARY OF THE INVENTION

In accordance with the invention claimed, an improved simple and inexpensive urine detector is provided for use in signalling unintentional urination.

It is, therefore, one object of this invention to provide a new and improved device for detecting unintentional urination.

Another object of this invention is to provide an improved urine detector which utilizes an easily detachable and replaceable elongated strip rendered conductive when wet.

A further object of this invention is to provide an improved moisture detector embodying an adhesively mounted strip which is rendered conductive when wet to complete a circuit to an alarm system.

A still further object of this invention is to provide an improved moisture detector, the housing of which forms a garment clip-on device.

A still further object of this invention is to provide a novel garment clip-on device utilizing a narrow strip adhesively mountable thereon of flexible material having spaced elongated electrodes on an inner face which are bridged by the release of urine to complete an alarm system in the device.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWING

The present invention may be more readily described by reference to the accompanying drawing, in which:

FIG. 1 is a perspective illustration of the detector device embodying the invention mounted on an undergarment in an operational configuration;

FIG. 2 is an enlarged perspective view of the garment clip on a portion of the detector device shown in FIG. 1;

FIG. 3 is a cross-sectional view of FIG. 2 taken along the line 3—3;

FIG. 4 is a cross-sectional view of FIG. 2 taken along the lines 4—4;

FIG. 5 is an enlarged partial view of the elongated strip shown in FIG. 1 illustrating more clearly the spaced conductive electrodes; and FIG. 6 is a diagrammatic block diagram of the electronic elements of the alarm system of the detector device shown in FIGS. 1-4.

DESCRIPTION OF THE PREFERRED EMBODIMENT

Referring more particularly to the drawing by characters of reference, FIG. 1 discloses the moisture detector 10 of this invention clipped on an undergarment 11 of a user. It should be noted that the detector 10 comprises a housing 12 conformed to provide a clamping means 13 for clipping on or over an exposed edge of a garment such as the waistband 14 of garment 11 and an elongated narrow strip of resilient flexible material 15 preferably having a narrow width of less than two inches and a thickness of about 0.125 inches. The strip may be made from a plastic material such as polyethylene, polypropylene, polytetrofluorethylene, nylon, or the like. The strip of material 15 is detachably connected at one end to housing 11 of the detector and along its length adhesively to the surface of the undergarment.

With reference to FIGS. 1 and 5, it will be seen that a pair of spaced electrodes 16 and 17 are enclosed within the body of the strip of material 15 over a major portion of the length extending at least from the end of the strip which is connected to the waistband 14. The electrodes emerge from the body of the strip over substantially the length of the strip on the garment exposed side of the strip.

As shown in FIGS. 1, 2 and 4 of the drawing, the electrodes of strip 15 are detachably connectable at one end of the strip to a pair of spring-type contacts 18 and 19 mounted within housing 12 and arranged to extend outwardly thereof through openings 20, 21 formed in the slot like indentation 22 in the outer surface of housing 12. These spring-type contacts are resiliently biased one into contact with the surface of each of the electrodes 16 and 17 when strip 15 and its surface 23 having an adhesive coating 24 arranged across its surface minus the exposed surface of electrodes 16 and 17 is physically pressed against the surface of the sloping bottom surface 22' of slot 22. When firmly held on the surface 22' of slot 22 of housing 12 and the remainder of surface 23 of strip 15 pressed against the outer surface 25 of the undergarment 11 device 10 when clamped to the undergarment in the manner shown in FIG. 1 will remain in place during use.

As shown in FIGS. 1, 2 and 4, housing 12 comprises a U-shaped configuration the spaced legs 12A and 12B of which form clamping means 13. Leg 12A forms a housing for electronic components which provide an audible sound when moisture provided by the wearer of the undergarment causes a short circuit at some point along the length of strip 15 to occur between its electrodes 16 and 17. The other leg 12B of housing 12 as shown in the drawings forms together with leg 12A the clamping means 13 wherein at least one leg such as leg 12B may be resiliently biased toward leg 12A.

Leg 12A forms a housing 26 having a cover 27 the exposed surface of which is formed to provide the slot 22 at the free end of leg 12A. Housing 26 is provided with a hollow interior within which is mounted the electronic components needed for providing the audible sound indicating an unintentional urination.

These components mounted on a circuit board 26A comprise an alarm device 28 which is energized by a transmitter means 29 that produces a signal to activate the alarm device when a trigger element such as urine electrically bridges the gap 30 between the electrodes 16 and 17. When this gap is bridged a signal is transmitted to a signal control means 31 which connects the transmitter means 29 to a battery 32 for producing the signal to energize the alarm device 28 in a well-known manner. The signal control means 31 is connected to the spring-type contacts 18 and 19 by suitable lead wires 33 and 34 for actuating the control means 31 in a normal manner. To aid in hearing the sound of the alarm device an opening 35 in the cover 27 of housing 26 is provided.

In use, the wearer or attendant places the undergarment or bedding, if used thereon, on or beneath the individual so that the exposed conductive electrodes 16 and 17 of strip 15 are in position to receive the flow of urine from the organ of urination. The strip 15 is then adhesively connected to the undergarment and one end to the surface 22' of slot 22 in housing 26. The transmitter through the signal control means 31 is electrically joined to spring-type contacts 18 and 19 at one end of strip 15.

When urine flows into the undergarment or bedding, the alarm will sound to draw attention to the fact that a clothing change is necessary due to the fact of urination.

The wearer or attendant can easily disconnect or remove the alarm device from the garment or bedding, change it and reconnect the same alarm device to the fresh undergarment or bedding merely utilizing a fresh new strip 15 of that material.

Although but one embodiment of the present invention has been illustrated and described, it will be apparent to those skilled in the art that various changes and modifications may be made therein without departing from the spirit of the invention or from the scope of the appended claims.

What is claimed is:

1. A device for detecting unintentional urination comprising:
    a housing for attaching to an undergarment,
    said housing containing an audio alarm means and having an outer surface thereof contoured to provide an indentation for receiving therein in surface contact therewith one end of a strip of flexible material,
    an elongated narrow strip of flexible, electrically insulating material having an inner face and an outer face,
    said strip containing a pair of spaced conductors extending longitudinally thereof along at least a part of its length with a surface of each conductor being exposed on the inner face of said strip,
    adhesive means on said inner face of said strip along at least a part of its length for adhering to the outer surface of the contour of said housing,
    a pair of contacts extending from within said housing through said surface of the contour for each engaging the exposed surface of a different one of said conductors, and
    means mounted within said housing for connection to said contacts and to said alarm means and actuated by urine occurring on the adhesive side of said strip bridging said electrodes which energizes said alarm means to provide an audible sound.

2. The device for detecting unintentional urination set forth in claim 1 wherein:
    said pair of contacts being spring biased for distortion under the pressure of said strip adhering to the contoured surface of said housing.

3. The device for detecting unintentional urination set forth in claim 1 wherein:
    said housing comprises a U-shaped configuration the legs of which are spaced a predetermined distance for forming a clamping means for slipping over the waistband of an undergarment.

4. The device for detecting unintentional urination set forth in claim 3 wherein:
    said strip comprises a plastic material having said conductors embedded therein with a surface of each conductor being exposed along said inner face of said strip.

5. The device for detecting unintentional urination set forth in claim 3 wherein:
    said legs of said housing are biased one toward the other.

6. The device for detecting unintentional urination set forth in claim 3 wherein:
    said means mounted within said housing and said alarm means are arranged in one leg of said housing.

7. The device for detecting unintentional urination set forth in claim 6 wherein:
    the contour of said housing is formed in the outer surface of said one leg of said housing.

8. The device for detecting unintentional urination set forth in claim 6 wherein:
    said one leg of said housing is provided with a snap-on cover which cover has the contour formed thereon.

* * * * *